(12) United States Patent
Xue et al.

(10) Patent No.: US 11,123,449 B1
(45) Date of Patent: Sep. 21, 2021

(54) MOBILE STERILIZATION SYSTEM, MOBILE EXECUTION SYSTEM, AND MOBILE ANALYSIS SYSTEM

(71) Applicants: Chio Kang Medical, Inc., Palo Alto, CA (US); Qiaokang Biotech (Guangdong) co., LTD., Guangzhou (CN)

(72) Inventors: Jianlong Xue, Guangzhou (CN); Dongxin Hou, Guangzhou (CN); Shengwei Hu, Guangzhou (CN); Xuzhong Liao, Guangzhou (CN); Xin Yin, Guangzhou (CN); Yecheng He, Guangzhou (CN); Guqun Ren, Guangzhou (CN); Yuhua Zou, Guangzhou (CN); Lixiong Feng, Palo Alto, CA (US)

(73) Assignees: Chio Kang Medical, Inc., Palo Alto, CA (US); Qiaokang Biotech (Guangdong) Co., LTD., Guangzhou (CN)

(*) Notice: Subject to any disclaimer, the term of this patent is extended or adjusted under 35 U.S.C. 154(b) by 0 days.

(21) Appl. No.: 17/004,730

(22) Filed: Aug. 27, 2020

Related U.S. Application Data

(63) Continuation of application No. PCT/CN2020/100120, filed on Jul. 3, 2020.

(51) Int. Cl.
*A61L 9/00* (2006.01)
*A61L 2/28* (2006.01)
(Continued)

(52) U.S. Cl.
CPC .................... *A61L 2/28* (2013.01); *A61L 2/07* (2013.01); *A61L 2/206* (2013.01); *A61L 11/00* (2013.01);
(Continued)

(58) Field of Classification Search
CPC .... A61L 2/0094; A61L 2/04; A61L 2202/123; A61L 2/20; A61L 2/24
(Continued)

(56) References Cited

U.S. PATENT DOCUMENTS

| 1,954,056 A | 4/1934 | Miller |
| 2,586,670 A | 2/1952 | Lambertsen |

(Continued)

FOREIGN PATENT DOCUMENTS

| CN | 1223166 A | 7/1999 |
| CN | 1397474 A | 2/2003 |

(Continued)

OTHER PUBLICATIONS

International Application No. PCT/CN2020/101140 as prepared by the Chinese International Searching Authority filed on Jul. 9, 2020, 59 pages.

(Continued)

*Primary Examiner* — Monzer R Chorbaji
(74) *Attorney, Agent, or Firm* — Adsero IP

(57) ABSTRACT

The present disclosure discloses a mobile sterilization system, a sterilization vehicle, a mobile execution system, a mobile preprocessing system, and a mobile analysis system. The mobile sterilization system includes a vehicle body, a sterilization system, a hydrothermal system, a gas supply system, a gas processing system, a humidification system, and a fresh air system, the sterilization system, the hydrothermal system, the gas supply system, the gas processing system, the humidification system, and the fresh air system being mounted on the vehicle body.

11 Claims, 8 Drawing Sheets

(51) Int. Cl.

| | | |
|---|---|---|
| *A61L 2/07* | (2006.01) | |
| *A61L 11/00* | (2006.01) | |
| *B60P 3/00* | (2006.01) | |
| *B01D 46/00* | (2006.01) | |
| *B01D 53/14* | (2006.01) | |
| *B01D 53/18* | (2006.01) | |
| *B01D 53/04* | (2006.01) | |
| *A61L 2/20* | (2006.01) | |
| *F24H 1/18* | (2006.01) | |
| *A61L 101/44* | (2006.01) | |

(52) U.S. Cl.
CPC ..... *B01D 46/0028* (2013.01); *B01D 46/0036* (2013.01); *B01D 53/04* (2013.01); *B01D 53/1487* (2013.01); *B01D 53/1493* (2013.01); *B01D 53/18* (2013.01); *B60P 3/00* (2013.01); *A61L 2101/44* (2020.08); *A61L 2202/11* (2013.01); *A61L 2202/122* (2013.01); *A61L 2202/13* (2013.01); *A61L 2202/14* (2013.01); *A61L 2202/15* (2013.01); *A61L 2202/16* (2013.01); *B01D 2252/205* (2013.01); *B01D 2252/504* (2013.01); *B01D 2252/60* (2013.01); *B01D 2253/102* (2013.01); *B01D 2257/70* (2013.01); *B01D 2259/455* (2013.01); *B01D 2279/00* (2013.01); *F24H 1/18* (2013.01)

(58) Field of Classification Search
USPC .................................................. 422/305, 307
See application file for complete search history.

(56) References Cited

U.S. PATENT DOCUMENTS

| | | | |
|---|---|---|---|
| 2,817,689 A | 12/1957 | White | |
| 3,022,054 A | 2/1962 | Kotzebue | |
| 3,572,391 A | 3/1971 | Hirsch et al. | |
| 3,598,543 A | 8/1971 | Crosby et al. | |
| 3,844,739 A | 10/1974 | Alfrey, Jr. | |
| 3,961,920 A | 6/1976 | Gilbert | |
| 3,997,633 A | 12/1976 | Leva et al. | |
| 4,112,054 A | 9/1978 | Feingold et al. | |
| 4,119,539 A | 10/1978 | Ettel et al. | |
| 4,134,425 A | 1/1979 | Gussefeld et al. | |
| 4,243,636 A | 1/1981 | Shiraki et al. | |
| 4,301,113 A | 11/1981 | Alguire et al. | |
| 4,517,167 A | 5/1985 | Popescu et al. | |
| 4,549,363 A | 10/1985 | Buonicore | |
| 4,555,251 A | 11/1985 | Jonsson | |
| 4,831,196 A | 5/1989 | Buonicore et al. | |
| 5,084,075 A | 1/1992 | Sircar | |
| 5,204,075 A | 4/1993 | Jain et al. | |
| 5,270,000 A * | 12/1993 | Goldner ................ A61L 11/00 |
| | | | 180/309 |
| 5,283,035 A | 2/1994 | Karthaus et al. | |
| 5,290,345 A | 3/1994 | Osendorf et al. | |
| 5,511,409 A | 4/1996 | Knaebel | |
| 5,522,808 A | 6/1996 | Skalla | |
| 5,607,652 A * | 3/1997 | Hellmuth ................ A61L 2/07 |
| | | | 422/300 |
| 5,641,455 A | 6/1997 | Rosenlund et al. | |
| 5,702,669 A | 12/1997 | Green et al. | |
| 5,741,470 A | 4/1998 | Wenzler | |
| 5,755,857 A | 5/1998 | Acharya et al. | |
| 5,779,773 A | 7/1998 | Cam et al. | |
| 5,964,927 A | 10/1999 | Graham et al. | |
| 6,156,101 A | 12/2000 | Naheiri | |
| 6,684,648 B2 | 2/2004 | Faqih | |
| 6,743,402 B2 | 6/2004 | Shimakawa | |
| 7,316,733 B1 | 1/2008 | Hedrick | |
| 7,625,535 B2 * | 12/2009 | Yamaguchi ............ A61L 2/07 |
| | | | 422/26 |
| 8,110,156 B2 | 2/2012 | Ricciardi et al. | |
| 8,431,085 B2 * | 4/2013 | Froderberg ............. B01J 3/04 |
| | | | 422/295 |
| 9,616,143 B2 | 4/2017 | Snyder et al. | |
| 10,987,443 B1 | 4/2021 | Hu et al. | |
| 2002/0046569 A1 | 4/2002 | Faqih | |
| 2002/0197194 A1 | 12/2002 | Machado et al. | |
| 2005/0145108 A1 | 7/2005 | Rubin | |
| 2006/0236860 A1 | 10/2006 | Sumida et al. | |
| 2006/0249027 A1 | 11/2006 | Adolphsen et al. | |
| 2007/0209383 A1 | 9/2007 | Hutton | |
| 2008/0078289 A1 | 4/2008 | Sergi et al. | |
| 2008/0080999 A1 | 4/2008 | Bondar | |
| 2008/0289591 A1 | 11/2008 | Tessier et al. | |
| 2010/0196194 A1 | 8/2010 | Voeten et al. | |
| 2011/0265644 A1 | 11/2011 | Swami et al. | |
| 2011/0283885 A1 | 11/2011 | Thiele | |
| 2012/0031268 A1 | 2/2012 | Yaghi et al. | |
| 2012/0298207 A1 * | 11/2012 | Woelk .................... C23C 16/52 |
| | | | 137/2 |
| 2014/0119989 A1 | 5/2014 | Hayashi | |
| 2014/0251130 A1 | 9/2014 | Sprinkle et al. | |
| 2014/0290162 A1 | 10/2014 | Tanimoto | |
| 2016/0010883 A1 | 1/2016 | Jomitz et al. | |
| 2017/0056813 A1 | 3/2017 | McMahon et al. | |
| 2019/0076776 A1 | 3/2019 | Mahecha-Botero et al. | |
| 2019/0151791 A1 | 5/2019 | Awadh et al. | |
| 2019/0175971 A1 | 6/2019 | Moore et al. | |
| 2020/0148655 A1 | 5/2020 | Duff et al. | |

FOREIGN PATENT DOCUMENTS

| | | |
|---|---|---|
| CN | 101224381 A | 7/2008 |
| CN | 101549241 A | 10/2009 |
| CN | 101773762 A | 7/2010 |
| CN | 201632182 U | 11/2010 |
| CN | 102173384 A | 9/2011 |
| CN | 102219642 A | 10/2011 |
| CN | 102302791 A | 1/2012 |
| CN | 102921570 A | 2/2013 |
| CN | 202802975 U | 3/2013 |
| CN | 202933710 U | 5/2013 |
| CN | 203183363 U | 9/2013 |
| CN | 103386141 A | 11/2013 |
| CN | 103394109 A | 11/2013 |
| CN | 103394278 A | 11/2013 |
| CN | 103657383 A | 3/2014 |
| CN | 103706233 A | 4/2014 |
| CN | 203507806 U | 4/2014 |
| CN | 203564952 U | 4/2014 |
| CN | 103800926 A | 5/2014 |
| CN | 103908688 A | 7/2014 |
| CN | 203749877 U | 8/2014 |
| CN | 203750388 U | 8/2014 |
| CN | 203750389 U | 8/2014 |
| CN | 104014227 A | 9/2014 |
| CN | 104275085 A | 1/2015 |
| CN | 104307008 A | 1/2015 |
| CN | 204261680 U | 4/2015 |
| CN | 204447972 U | 7/2015 |
| CN | 104815535 A | 8/2015 |
| CN | 105132060 A | 12/2015 |
| CN | 105327665 A | 2/2016 |
| CN | 105664822 A | 2/2016 |
| CN | 205300112 U | 6/2016 |
| CN | 210721130 U | 6/2016 |
| CN | 106139199 A | 11/2016 |
| CN | 106421844 A | 2/2017 |
| CN | 106475021 A | 3/2017 |
| CN | 106582126 A | 4/2017 |
| CN | 206443946 U | 8/2017 |
| CN | 206535551 U | 10/2017 |
| CN | 206853397 U | 1/2018 |
| CN | 107677016 A | 2/2018 |
| CN | 207169397 U | 4/2018 |
| CN | 207187436 U | 4/2018 |
| CN | 207356290 U | 5/2018 |
| CN | 207745676 U | 8/2018 |
| CN | 207913454 U | 9/2018 |
| CN | 108607511 A | 10/2018 |

(56) References Cited

FOREIGN PATENT DOCUMENTS

| | | |
|---|---|---|
| CN | 208047841 U | 11/2018 |
| CN | 208218734 U | 12/2018 |
| CN | 109382064 A | 2/2019 |
| CN | 208448985 U | 2/2019 |
| CN | 208893903 U | 5/2019 |
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| JP | 2013172790 A | 10/2016 |
| JP | 2010259648 A | 5/2018 |
| WO | WO2011002277 A1 | 1/2011 |
| WO | WO-2019-136504 A1 | 7/2019 |
| WO | WO2019236249 A1 | 12/2019 |

OTHER PUBLICATIONS

U.S. Appl. No. 17/012,857, TrackOne Bypass CON Application filed Sep. 4, 2020, 148 pages.
International Application No. PCT/CN2020/100143 as prepared by the Chinese International Searching Authority filed on Jul. 3, 2020, 25 pages.
U.S. Appl. No. 17/002,500, TrackOne Bypass CON Application filed Aug. 25, 2020, 61 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
U.S. Appl. No. 17/002,529, TrackOne Bypass CON Application filed Aug. 25, 2020, 64 pages.
International Application No. PCT/CN2020/100119 as prepared by the Chinese International Searching Authority filed on Jul. 3, 2020, 29 pages.
U.S. Appl. No. 17/002,540, TrackOne Bypass CON Application filed Aug. 25, 2020, 89 pages.
International Application No. PCT/CN2020/100120 as prepared by the Chinese International Searching Authority filed on Jul. 3, 2020, 28 pages.
International Application No. PCT/CN2020/101142 as prepared by the Chinese International Searching Authority filed on Jul. 9, 2020, 29 pages.
U.S. Appl. No. 17/012,864, TrackOne Bypass CON Application filed Sep. 4, 2020, 78 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
U.S. Appl. No. 17/004,930, TrackOne Bypass CON Application filed Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed on Jul. 3, 2020, 35 pages.
U.S. Appl. No. 17/004,971, TrackOne Bypass CON Application filed Aug. 27, 2020, 75 pages.
U.S. Appl. No. 17/012,857 Non-Final Office Action, dated Nov. 24, 2020, 13 pages.
U.S. Appl. No. 17/002,540 Office Action-Restriction Requirement, dated Dec. 1, 2020, 7 pages.
U.S. Appl. No. 17/002,500 Non-Final Office Action dated Dec. 8, 2020, 109 pages.
Kahm et al., 2018 "Lyapunov exponents with Model Predictive Control for exothermic batch reactors" IFAC—PapersOnline, 51, 417-422.
U.S. Appl. No. 17/004,971 Office Action-Restriction Requirement, dated Dec. 9, 2020, 6 pages.
U.S. Appl. No. 17/002,523 Notice of Allowance, dated Dec. 17, 2020, 35 pages.
U.S. Appl. No. 17/004,930 Office Action-Restriction Requirement, dated Dec. 18, 2020, 8 pages.
U.S. Appl. No. 17/002,540 Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500 Final Office Action dated Feb. 8, 2021, 57 pages.
U.S. Appl. No. 17/004,971 Notice of Allowance, dated Feb. 8, 2021, 30 pages.
U.S. Appl. No. 17/002,529 Non-Final Office Action-Restriction Requirement dated Feb. 17, 2021, 11 pages.
U.S. Appl. No. 17/012,857 Notice of Allowance, dated Mar. 1, 2021, 26 pages.
U.S. Appl. No. 17/002,540 Final Office Action, dated Mar. 26, 2021, 36 pages.
U.S. Appl. No. 17/002,500 Non-Final Office Action dated Apr. 14, 2021, 89 pages.
U.S. Appl. No. 17/002,540 Notice of Allowance, dated Apr. 26, 2021, 21 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.

(56) References Cited

OTHER PUBLICATIONS

U.S. Appl. No. 17/004,930 Notice of Allowance, dated Apr. 28, 2020, 35 pages.
U.S. Appl. No. 17/004,903 Notice of Allowance, dated May 17, 2021, 20 pages.
U.S. Appl. No. 17/002,529 Notice of Allowance, dated May 3, 2021, 30 pages.
U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/012,857, Notice of Allowance, dated Jun. 28, 2021, 21 pages.
U.S. Appl. No. 17/002,500, Notice of Allowance dated Jul. 8, 2021, 27 pages.

* cited by examiner

MOBILE STERILIZATION SYSTEM, MOBILE EXECUTION SYSTEM, AND MOBILE ANALYSIS SYSTEM

CROSS-REFERENCE TO RELATED PATENT APPLICATIONS

This application is a continuation of International Application No. PCT/CN2020/100120, filed on Jul. 3, 2020, which is incorporated herein by reference in its entirety for all purposes.

TECHNICAL FIELD

The present disclosure relates to the technical field of sterilization technology, and more particularly, to a mobile sterilization system, a mobile execution system, a mobile preprocessing system, and a mobile analysis system.

BACKGROUND

Major epidemics of infectious diseases caused by pathogenic microorganisms are sudden public health events that seriously endanger the public health. Such events often take people off guard and can easily lead to social panic. During the response to an epidemic, it is necessary to treat a large amount of medical waste and domestic pollutants containing pathogenic microorganisms.

However, at present, the common sterilization methods in hospitals, laboratories, and living spaces are mainly steam sterilization, ultraviolet lamp sterilization, etc. Some pathogenic microorganisms (e.g., budding spores) cannot be completely eliminated due to limitations such as conditions of use and methods of use. In addition, the corresponding sterilization equipment is typically small in size and does not allow for large-scale medical waste treatment. Further, the medical waste cannot generally be treated on site, and needs to be transported to a specific treatment site, which can easily lead to wider pollution or contamination.

Ethylene oxide is a broad-spectrum, highly effective sterilizer that can kill most pathogenic microorganisms. Ethylene oxide low temperature sterilization is a sterilization process that is currently widely used. The ethylene oxide sterilization process generally includes the three steps of preprocessing, sterilization, and analysis. In the preprocessing step, the preprocessing operations, such as pre-heating and/or pre-humidification, are performed on the items to be sterilized. In the sterilization step, ethylene oxide is used to sterilize the items that have been preprocessed. In the analysis step, the sterilized items that have undergone the ethylene oxide sterilization step are analyzed to reduce the ethylene oxide content on the sterilized items. The current ethylene oxide sterilization process requires a lot of equipment, the operation is relatively complicated, and the mobility is poor, which cannot meet market demands.

Hence, there is a need for more robust and scalable solutions for implementing sterilization technologies, and, more particularly, for implementing a mobile sterilization system, a mobile execution system, a mobile preprocessing system, and a mobile analysis system.

SUMMARY

The present disclosure provides a mobile sterilization system including a vehicle body, a sterilization system, a hydrothermal system, a gas supply system, a gas processing system, a humidification system, and a fresh air system mounted on the vehicle body. The sterilization system includes a sterilization tank used to contain items to be sterilized, and a heat supply device comprising a heating chamber surrounding the sterilization tank. The hydrothermal system comprises a water heating tank connected to the heating chamber of the heat supply device through a hot water outlet pipe and a hot water return pipe. The gas supply system comprises a sterilization gas source and a gasifier, wherein a gas inlet of the gasifier is connected to the sterilization gas source through a sterilization gas inlet pipeline, a gas outlet of the gasifier is connected to the sterilization tank through a sterilization gas outlet pipeline, and a water circulation pipe is disposed between the gasifier and the water heating tank. The gas processing system comprises a fan, a vacuum pump, and a gas processing device, wherein an inlet of the gas processing device is connected to the sterilization tank through a gas processing pipe, the fan and the vacuum pump are mounted on the gas processing pipe, and the gas processing device is configured to process a sterilization exhaust gas that is input from the gas processing pipe. The humidification system comprises a steam generator, wherein a gas outlet of the steam generator is connected to the sterilization tank through a humidification pipe. The fresh air system comprises an air inlet pipeline connected to the sterilization tank, and an air filter mounted on the air inlet pipeline.

The present disclosure further provides a sterilization vehicle comprising a vehicle body, a sterilization tank, a heat supply device, and an air inlet system. The sterilization tank is configured to contain items to be sterilized, is connected to a sterilization gas pipeline to receive a sterilization gas, and is connected to a gas processing pipe to output a sterilization exhaust gas. The heat supply device comprises a heating chamber surrounding the sterilization tank. The air inlet system comprises an air inlet pipeline connected to the sterilization tank, and an air filter mounted on the air inlet pipeline.

The present disclosure further provides a mobile execution system, the mobile execution system comprising a hydrothermal system, a gas supply system, a gas processing system, and a humidification system. The hydrothermal system comprises a water heating tank, a hot water outlet pipe, and a hot water return pipe. Each of the hot water outlet pipe and the hot water return pipe is connected to the water heating tank. The gas supply system comprises a sterilization gas source and a gasifier. A gas inlet of the gasifier is connected to the sterilization gas source through a sterilization gas inlet pipeline. A gas outlet of the gasifier is provided with a sterilization gas outlet pipeline. A water circulation pipe is disposed between the gasifier and the water heating tank. The gas processing system comprises a gas processing device. An inlet of the gas processing device is connected to a gas processing pipe. A first air extraction device is mounted on the gas processing device. The gas processing device is configured to process a sterilization exhaust gas that is input from the gas processing pipe. The humidification system comprises a steam generator. A gas outlet of the steam generator is connected to the sterilization tank.

The present disclosure further provides a mobile preprocessing system comprising a detachable preprocessing chamber and a vehicle-mounted system suitable to be mounted on a vehicle. The detachable preprocessing chamber is configured to contain the items to be sterilized. A temperature and humidity detector is disposed inside the detachable preprocessing chamber. A humidification spray head is disposed inside the preprocessing chamber and on a top portion of the preprocessing chamber. A water heating plate is disposed inside the preprocessing chamber and on a bottom portion of the preprocessing chamber. The vehicle-mounted system comprises a heating system and a humidification system. The heating system comprises a water heating tank and a heater. The water heating tank is connected to the water heating plate through a water heating inlet pipe and a water heating return pipe. The humidification system comprises a water supplementing pipe, an atomizer, and a humidification pipe that are connected in sequence. The humidification pipe is connected to the humidification spray head.

The present disclosure further provides a mobile analysis system, comprising a vehicle-mounted system mounted on a vehicle and a detachable analysis chamber configured to contain sterilized items. The vehicle-mounted system comprises a harmless gas processing device and a fresh air system. The harmless gas processing device comprises a tank body and a reaction liquid contained in the tank body. A top portion of the detachable analysis chamber is connected to a bottom portion of the harmless gas processing device through an exhaust pipe. The fresh air system comprises a gas inlet pipe and an air filter disposed on the air inlet pipe, and the gas inlet pipe is connected to the detachable analysis chamber.

Each device involved in the sterilization solution provided by the present disclosure has the advantages of flexible structure, strong mobility, and relatively simple operation. In particular, during sudden epidemics, the technical solution of the present disclosure can respond quickly and provide high-efficiency sterilization for a large number of items that are disposed in a large space and/or disposed in multiple spaces located over a wide geographic area.

These and other objects, advantages, purposes, and features will become apparent upon review of the following detailed description in conjunction with the drawings.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 1:
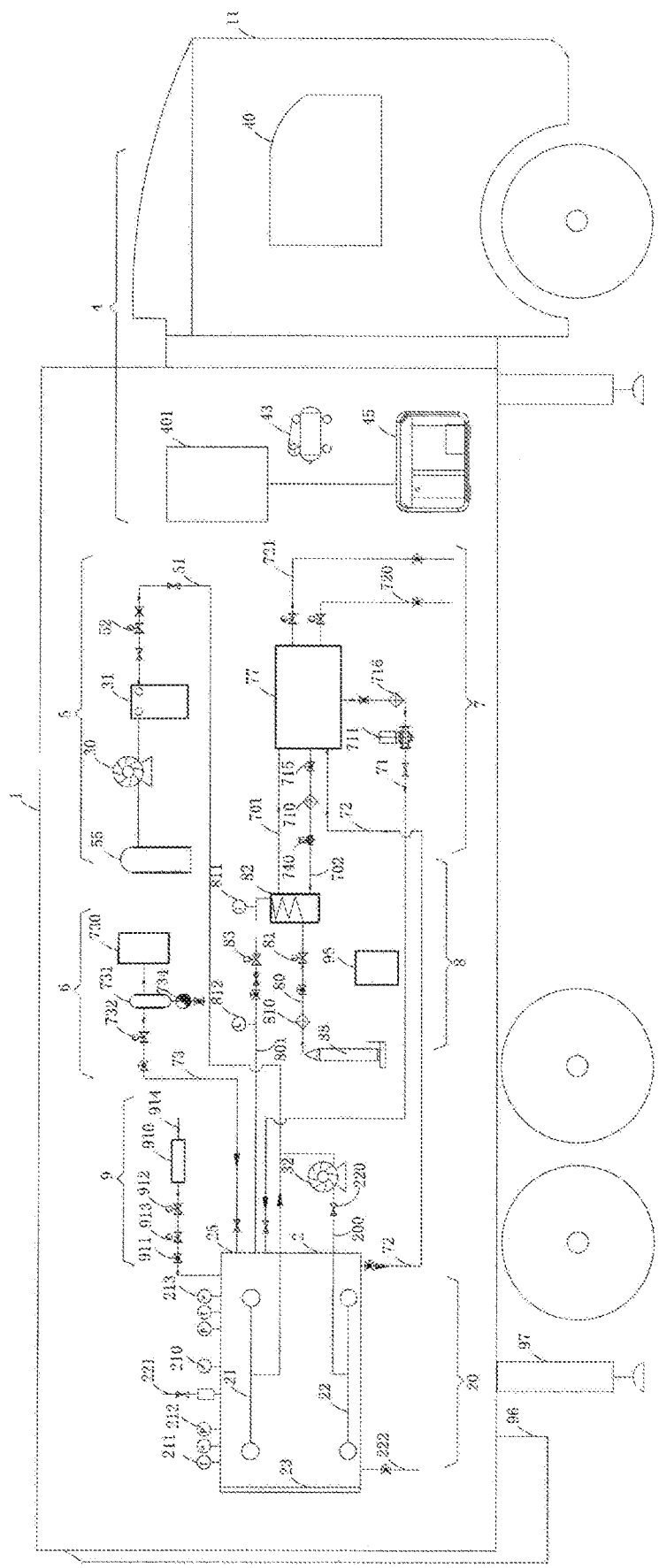
FIG. 1 is a schematic diagram of a mobile sterilization system in an embodiment.

FIG. 1 illustrates an embodiment of a mobile sterilization system including a cab 11 and a vehicle body 1.

An interior of the vehicle body 1 is equipped with a power supply control system 4, a sterilization system, a gas supply system 8, a sterilization gas processing system 5, a constant temperature incubator 95, a hydrothermal system 7, a fresh air system 9, a humidification system 6, and the like. Four support systems 97 are mounted on four corners of the bottom portion of the vehicle body 1. A lifting device 96 is mounted on a rear portion of the vehicle body 1.

The power supply control system 4 includes a driving system 40, a control system 401, an air compression device 43, and a power supply system 45. For example, the power supply system 45 might be a diesel generator.

The driving system 40 is disposed in the cab 11. The control system 401, the air compressor 43, and the power supply system 45 are disposed in the vehicle body 1 located behind the cab 11. The power supply system 45 is used to supply power to the components of the sterilization tank 2, the humidification system 6, the fresh air system 9, the gas supply system 8, the sterilization gas processing system 5, and the hydrothermal system 7. The control system 401 is electrically connected to the electronic control components of the sterilization tank 2, the fresh air system 9, the sterilization gas processing system 5, the hydrothermal system 7, a humidification system 6, and the like. The control system 401 can control the on/off state and operation of each electronic control component, and is used to receive signals from various sensors. The air compressor 43 is used to provide pressurized air for a pneumatic ball valve (e.g., pneumatic ball valves 52, 81, 732, or 913, and the like).

The sterilization tank 2 has a volume in the range of 6 m$^3$ to 20 m$^3$. A safety valve 221 is mounted on the top portion of the sterilization tank 2, and plays the role of safety protection in the system, by venting to prevent over-pressurization in the sterilization tank 2. A rear wall of the sterilization tank 2 is provided with a sealing door 23 through which the items enter and exit the interior chamber of the sterilization tank 2, and the items are sterilized in the interior chamber of the sterilization tank 2. A bottom portion of the sterilization tank 2 is provided with a water outlet pipe 222.

A gas circulation pipeline system 20 is mounted on the sterilization tank 2. The gas circulation pipeline system 20 has four vents, two of which are located on a lower portion of the sterilization tank 2, and the other two vents are located on an upper portion of the sterilization tank 2. The two vents on the upper portion are connected to each other through a gas outlet pipe 21 outside the sterilization tank 2, and the two vents in the lower position are connected to each other through a gas inlet pipe 22 outside the sterilization tank 2. A gas circulation pipe 200 is connected between the gas outlet pipe 21 and the gas inlet pipe 22, and a fan 32 is mounted in the gas circulation pipe 200. A first control valve 220 is mounted on the gas circulation pipe 200, and is located downstream of an airflow of the fan 32. The sterilization tank 2 is provided with one or more sensors, the one or more sensors including, without limitation, at least one of a plurality of humidity sensors 213, a plurality of pressure sensors 212, a plurality of temperature sensors 211, or a plurality of ethylene oxide concentration detectors 210, and/or the like.

A heat supply device 25 is further provided outside the sterilization tank 2. The heat supply device 25, in some cases, may be a heating jacket covering the sterilization tank 2. The heat supply device 25 forms a heating chamber surrounding the sterilization tank 2, and hot water flows in the heating chamber to heat the sterilization tank 2. It should be understood that the heating chamber may completely surround the sterilization tank 2 or may only surround a part of the sterilization tank 2.

A gas inlet pipeline 914 of the fresh air system 9 is connected to the outside portion of the sterilization tank 2. An air filter 910, an electric proportional valve 912, and a pneumatic ball valve 913 of the fresh air system 9 are sequentially connected to the gas inlet pipeline 914.

The gas supply system 8 includes an ethylene oxide gas cylinder (or sterilization gas source) 88, a sterilization gas inlet pipeline 80, a filter 810, a gasifier 82, a sterilization gas outlet pipeline 801, a temperature sensor 811, a flow sensor 812, and a plurality of valves. The ethylene oxide gas cylinder 88, the filter 810, and the gasifier 82 are sequentially connected to the sterilization gas inlet pipeline 80, so that the gas inlet of the gasifier 82 is connected to the ethylene oxide gas cylinder 88 through the sterilization gas inlet pipeline 80. The temperature sensor 811 and the flow sensor 812 are sequentially connected to the sterilization gas outlet pipeline 801. The gas outlet of the gasifier 82 is connected to an end of the sterilization gas outlet pipeline 801, and the other end of the sterilization gas outlet pipeline 801 is connected to the front wall of the sterilization tank 2. The sterilization gas pipeline in the gasifier 82 is folded or bent (or forms a spiral), and is connected to each of the sterilization gas inlet pipeline 80 and the sterilization gas outlet pipeline 801. A pneumatic ball valve 81 is disposed between the filter 810 and the gasifier 82, and an electric proportional valve 83 is disposed between the temperature sensor 811 and the flow sensor 812.

The sterilization gas pipeline in the gasifier 82 is folded or bent, which increases the heating and gasification time of the sterilization gas in the gasifier 82. The hot water output by the hydrothermal system 7 is used to heat and gasify the sterilization gas in the gasifier 82, which results in safer operations. In some cases, electric proportional valves (like electric proportional valves 83, or the like) may be disposed on both sides of the gasifier 82 (not just on the sterilization gas outlet side, as shown in FIG. 1), which facilitates the accurate control of the gas intake speed. The flow sensor 812 is beneficial to accurately control and monitor the gas inflow.

The sterilization gas processing system 5 includes a gas processing device 55, an extraction device (such as fan 30, vacuum pump 31, and the like), a gas processing pipe 51, a pneumatic ball valve 52, and a plurality of other valves. The gas processing device 55, the fan 30, the vacuum pump 31, and the pneumatic ball valve 52 are sequentially connected to the gas processing pipe 51. The inlet of the gas processing device 55 is connected to the sterilization tank 2 through the gas processing pipe 51. In particular, the inlet of the gas processing pipe 51 is connected to the gas circulation pipe 200 that is disposed outside the sterilization tank 2.

The sterilization gas processing system 5 is used to perform harmless gas processing on the sterilization gas, which can remove the ethylene oxide in the sterilization exhaust gas, so that the exhaust gas meets safety standards and causes no pollution to the environment.

A liquid absorption filler and a solid absorption filler are disposed in the gas processing device 55. A liquid absorption filler may be a solution obtained by mixing oleic acid, sulfated castor oil, sodium chloride, potassium hydroxide, and calcium hydroxide in a molar ratio of 1:1:0.01:0.01:0.01. The solid absorbent filler may be coconut shell activated carbon.

The hydrothermal system 7 includes a water inlet pipe 721, a water outlet pipe 720, a water heating tank 77, a water pump 711, a water pump 740, a filter 710, a hot water outlet pipe 71, and a hot water return pipe 72.

Water circulation pipes 701, 702 are disposed between the water heating tank 77 and the gasifier 82. The water circulation pipe 702 is used to fill the gasifier 82 with hot water. The valve 715, the filter 710, and the water pump 740 are sequentially disposed in the water circulation pipe 702. The water circulation pipe 701 is used to recycle the hot water passing through the gasifier 82, by returning the hot water to the water heating tank 77. The water inlet pipe 721 and the water outlet pipe 720 are respectively connected to the upper and lower portions of the front wall of the water heating tank 77. The water inlet pipe 721 can be connected to an external water source (e.g., tap water, or the like), while the water outlet pipe 720 is used to drain the water heating tank 77. The hot water outlet pipe 71 and the hot water return pipe 72 are connected between the heating chamber of the heat supply device 25 of the sterilization tank 2 and the water heating tank 77, thus forming a water heating circulation circuit for the sterilization tank 2. The water heating tank 77 heats the sterilization tank 2 by using hot water. One end of the hot water outlet pipe 71 is connected to the bottom portion of the water heating tank 77, and the other end of the hot water outlet pipe 71 is connected to the heat supply device 25 on the upper portion of the front wall of the sterilization tank 2. The end of the hot water outlet pipe 71 close to the water heating tank 77 is provided with a filter 716 and the water pump 711. Valves are provided on the hot water outlet pipe 71 between the water pump 711 and the sterilization tank 2, and between the water heating tank 77 and the filter 716. One end of the hot water return pipe 72 is connected to the lower portion of the rear wall of the water heating tank 77, and the other end of the hot water return pipe 72 is connected to the heat supply device 25 on the bottom portion of the sterilization tank 2. A liquid level sensor is further mounted in the water heating tank 77 to monitor the liquid level in the water heating tank 77.

The humidification system 6 includes a humidification pipe 73, a hydrophobic valve 734, a pneumatic ball valve 732, a steam filter 731, and a steam generator 730. The pneumatic ball valve 732, the steam filter 731, and the steam generator 730 are disposed on the humidification pipe 73. The hydrophobic valve 734 is disposed on the bottom portion of the steam filter 731. One end of the humidification pipe 73 is connected to the side wall of the sterilization tank 2. The pneumatic ball valve 732 and a valve are disposed between the steam generator 730 and the sterilization tank 2.

The sterilization tank 2 is provided with one or more sensors, the one or more sensors including, without limitation, at least one of a humidity sensors 213, a pressure sensors 212, a temperature sensors 211, or an ethylene oxide concentration detector 210, and/or the like, that are used to monitor the interior chamber environment of sterilization tank 2 and are beneficial to monitor the entire sterilization process in real time. The gas circulation pipeline 200 is mounted outside the sterilization tank 2 to increase the uniformity of the distribution of the sterilization gas and to improve the sterilization effect.

Furthermore, the constant temperature incubator 95 may be a constant temperature incubator for an ethylene oxide sterilization biological indicator, which may perform constant temperature incubation for the ethylene oxide sterilization biological indicator arranged in the sterilizer in the sterilization process to detect the sterilization effect.

The present disclosure further provides a method for using the above-described mobile sterilization system, and the method includes the following steps:

(1) The mobile sterilization system moves or is driven to quickly reach the designated location.

(2) The mobile sterilization system may not carry the ethylene oxide gas cylinder 88 during moving, in which case, the ethylene oxide gas cylinder 88 may be delivered to the designated location by professionals and other vehicles. After that, the ethylene oxide gas cylinder 88 is connected to the sterilization gas inlet pipeline 80. The mobile sterilization system is thus mobile and flexible.

(3) When the sterilization work begins, the power supply system 45 and the control system 401 are switched on in sequence. All systems are powered by the power supply system 45, and the control system 401 controls the power switching and operation of each component.

(4) The water inlet pipe 721 is connected to an external water source (e.g., tap water source, or the like), and the water heating tank 77 is filled with water through the water inlet pipe 721.

(5) Heating of the water heating tank 77 is started. After the water temperature reaches the working temperature (about 60° C. to about 80° C.), the water pumps 740 and 711 are switched on. The cyclic heating for the heating supply device 25 of the sterilization tank 2 and the gasifier 82 are performed. Monitoring of the temperature in the sterilization tank 2 by the temperature sensor 211 is started. Adjustment of the water temperature of the water heating tank 77 or adjustment of the circulation speed of the circulation pump 711 is also started, and allowing the temperature in the sterilization tank 2 to be in the range of 50° C. to 60° C.

(6) The sealing door 23 is opened, the lifting device 96 is used to load the item to be sterilized into the sterilization tank 2, and the sealing door 23 is subsequently closed.

(7) The vacuum pump 31, the pneumatic ball valve 52, and the exhaust fan 30 are simultaneously turned on or opened, as appropriate, evacuating the sterilization tank 2 to −80 kPa to −30 kPa. The vacuum pump 31, the pneumatic ball valve 52, and the exhaust fan 30 are subsequently turned off or closed, as appropriate.

(8) The steam generator 730 and the pneumatic ball valve 732 are turned on or opened, as appropriate. The steam generator 730 provides the water vapor, which enters the sterilization tank 2 for humidification through the steam filter 731. The humidity sensor 213 monitors the humidity in the sterilization tank 2. After the humidity sensor 213 detects humidity in the sterilization tank 2 in the range of 50% to 70%, the steam generator 730 and the pneumatic ball valve 732 are turned off or closed, as appropriate.

(9) The stop valve on the ethylene oxide gas cylinder 88, the pneumatic ball valve 81, and the electric proportional valve 83 are opened, allowing the ethylene oxide in the ethylene oxide gas cylinder 88 to pass through the sterilization gas inlet pipeline 80, to be heated and gasified by the gasifier 82, and then to fill the sterilization tank 2. The ethylene oxide concentration detector 210 in the sterilization tank 2 detects the concentration of the ethylene oxide in the sterilization tank 2, while the temperature sensor 811 and the flow sensor 812 on the sterilization gas outlet pipe 801 respectively monitor the temperature and the flow rate of the sterilization gas (i.e., the ethylene oxide, or the like) in the sterilization gas outlet pipe 801 (with the working temperature ranging from 50° C. to 60° C.). After the gas filling has been completed, the pneumatic ball valve 81 and the electric proportional valve 83 are closed, and the circulation pump 740 is turned off.

(10) The sterilization process is performed, using the hot water to continuously heat the sterilization tank 2, using the circulation pump 711 to make the temperature of the sterilization tank 2 constant, using the fan 32 to circulate the ethylene oxide sterilization gas in the sterilization tank 2, using the temperature sensor 211 to monitor the temperature in the sterilization tank 2, using the humidity sensor 213 to monitor the humidity in the sterilization tank 2 (with the working humidity ranging from 50% to 70%), and using the pressure sensor 212 to monitor the pressure in the sterilization tank 2 (with the working pressure ranging from 30 kPa to 50 kPa). The duration of the sterilization process ranges from 3 to 8 hours.

(11) After sterilization has been completed, the sterilization process is terminated, and the replacement process and the harmless gas processing of ethylene oxide in the sterilization tank 2 is started.

(12) The vacuum pump 31, the pneumatic ball valve 52, and the exhaust fan 30 are turned on or opened, as appropriate, to evacuate the interior of the sterilization tank 2, drawing the ethylene oxide sterilization waste gas into the sterilization gas processing device 55 for harmless gas processing. When the pressure in the sterilization tank 2 ranges from −80 kPa to −30 kPa, the vacuum pump 31, the pneumatic ball valve 52, and the exhaust fan 30 are turned off or closed, as appropriate. The electric proportional valve 912 and the pneumatic ball valve 913 are opened, thereby filling the sterilization tank 2 with fresh air that is filtered by the air filter 910. Once the sterilization tank 2 has been filled with filtered fresh air, the electric proportional valve 912 and the pneumatic ball valve 913 are closed, and the vacuum pump 31, the pneumatic ball valve 52, and the exhaust fan 30 are once again turned on or opened, as appropriate, to draw out the gas in the sterilization tank 2 once more for the harmless gas processing of the sterilization gas. After replacing the ethylene oxide sterilization exhaust gas in the sterilization tank 2 with the filtered fresh air several times, the sterilization tank 2 is refilled with fresh air to allow the pressure in the sterilization tank 2 to be restored to atmospheric pressure. Subsequently, the vacuum pump 31, the pneumatic ball valve 52, the exhaust fan 30, the electric proportional valve 912, and the pneumatic ball valve 913 are turned off or closed, as appropriate.

(13) The sealing door 23 is opened, the sterilized items are taken out of the sterilization tank 2, and the sealing door 23 is subsequently closed.

(14) The circulation pump 711, the water heating tank 77, and the power supply system 45 are turned off.

The process described above can remove 99.99% of ethylene oxide in the sterilization exhaust gas.

In the above-described mobile sterilization system, all systems are mounted on the vehicle body 1, which is flexibly configurable and mobile, and expands the application scenarios of the sterilizer. When the mobile sterilization system is parked, the support systems 97 can increase the stability of the vehicle body 1 and maintain the vehicle body 1 in a level position. The vehicle body 1 is equipped with the lifting device 96 for loading and unloading the sterilized items, which reduces manpower and improves the working efficiency of the mobile sterilization system. The mobile sterilization system can quickly reach the epidemic field, can perform pre-heating, pre-humidifying, sterilization, and analysis of the medical waste on site. In this manner, the mobile sterilization system can effectively eliminate various microorganisms, while also performing harmless gas processing of the sterilization exhaust gas to avoid polluting the environment.

Figure 2:
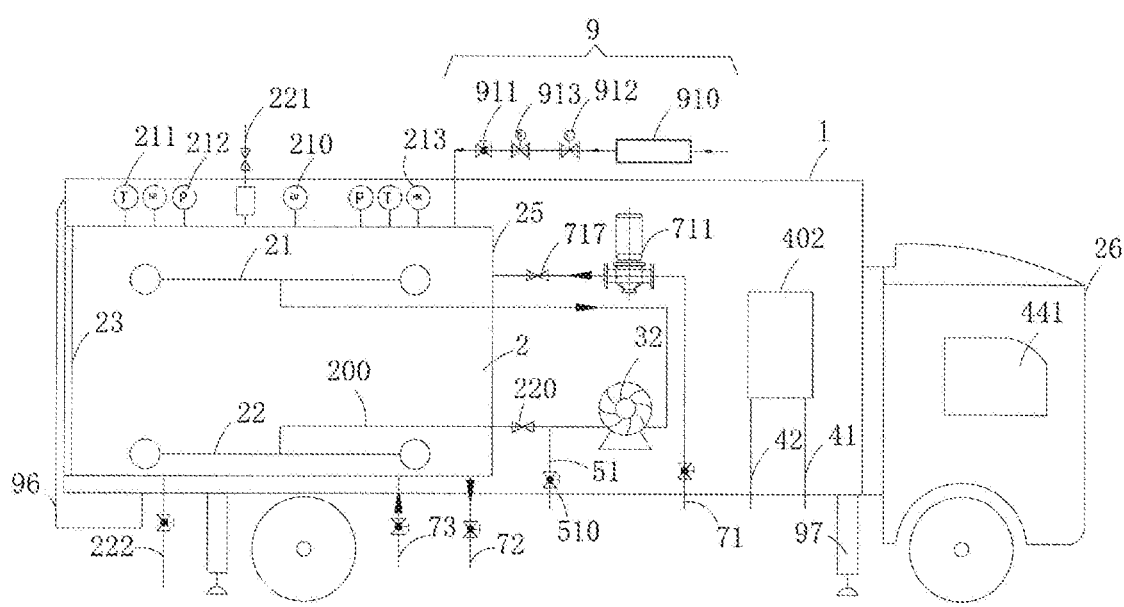
FIG. 2 is a schematic diagram of a small sterilization vehicle in an embodiment.

FIG. 2 illustrates a small sterilization vehicle according to an embodiment, which includes a sterilization system, a cab 26, and a vehicle body 1. The sterilization system is mounted on the vehicle body 1.

Support systems 97 are each mounted on one of the four corners of the lower portion of the vehicle body 1, and a lifting device 96 is mounted on the rear portion of the vehicle body. A driving system 441 is disposed in the cab 26.

The sterilization system includes, without limitation, a sterilization tank 2, a water pump 711, a fan 32, a control system 402, an air inlet system 9, and the like.

The sterilization tank 2 is used to contain items to be sterilized. The sterilization tank 2 is connected to a sterilization gas pipeline (e.g., gas processing pipe 51 as described below, or the like) to receive the sterilization gas, for example, ethylene oxide gas. The sterilization tank 2 is connected to a gas processing pipe 51 to output the sterilization exhaust gas. The top portion of the sterilization tank 2 is provided with a safety valve 221 and an air inlet pipeline. The top portion of the sterilization tank 2 is also provided with one or more sensors, the one or more sensors including, without limitation, at least one of a plurality of temperature sensors 211, a plurality of humidity sensors 213, a plurality of pressure sensors 212, or a plurality of ethylene oxide concentration detectors 210, and/or the like, that are used to detect the interior environment of the sterilization tank 2. An air filter 910, an electric proportional valve 912, a pneumatic ball valve 913, and a stop valve 911 are sequentially connected to the air inlet pipeline of the air inlet system.

The rear wall of the sterilization tank 2 is provided with a sealing door 23. The bottom portion of the sterilization tank 2 is provided with a humidification pipe 73, a hot water return pipe 72, and a water outlet pipe 222. The humidification pipeline 73, the hot water return pipeline 72, and the water outlet pipe 222 are provided with valves.

The side wall of the sterilization tank 2 has four vents, two of which are located on a lower portion of the sidewall of the sterilization tank 2, and the other two vents are located on the upper portion of the sidewall of the sterilization tank 2. The two vents on the upper portion are connected to each other through a gas outlet pipe 21, and the two vents in the lower portion are connected to each other through a gas inlet pipe 22. A gas circulation pipe 200 is connected between the gas outlet pipe 21 and the gas inlet pipe 22, and a fan 32 is mounted in the gas circulation pipe 200. Between the fan 32 and the gas inlet pipe 22 is provided a control valve 220 mounted on the gas circulation pipe 200 and located downstream of an airflow of the fan 32. The inlet end of the gas processing pipe 51 is connected to the gas circulation pipe 200 between the control valve 220 and the fan 32. The gas processing pipe 51 is provided with a control valve 510. By controlling the opening and closing of one or both of the control valve 220 and the control valve 510, the sterilization gas can be controlled to enter the sterilization tank 2 for sterilization, or can be discharged from the sterilization tank into the gas processing pipe 51 for harmless gas processing.

A heat supply device 25 is further disposed outside the sterilization tank 2. The heat supply device 25, in some cases, may be a heating jacket covering the sterilization tank 2. The heat supply device 25 forms a heating chamber surrounding the sterilization tank 2, and hot water flows in the heating chamber to heat the sterilization tank 2. It should be understood that the heating chamber may completely surround the sterilization tank 2 or may only surround a part of the sterilization tank 2. The heat supply device 25 is connected to the hot water inlet pipe 71, and the hot water inlet pipe 71 is provided with a valve 717 and the water pump 711.

The control system 402 is disposed on the vehicle body 1 behind the cab 26, and receives the control signal output from a mobile execution system and returns a feedback signal through a signal line 41, and receives the electric power output from the mobile execution system through an electric transmission line 42.

Figure 3:
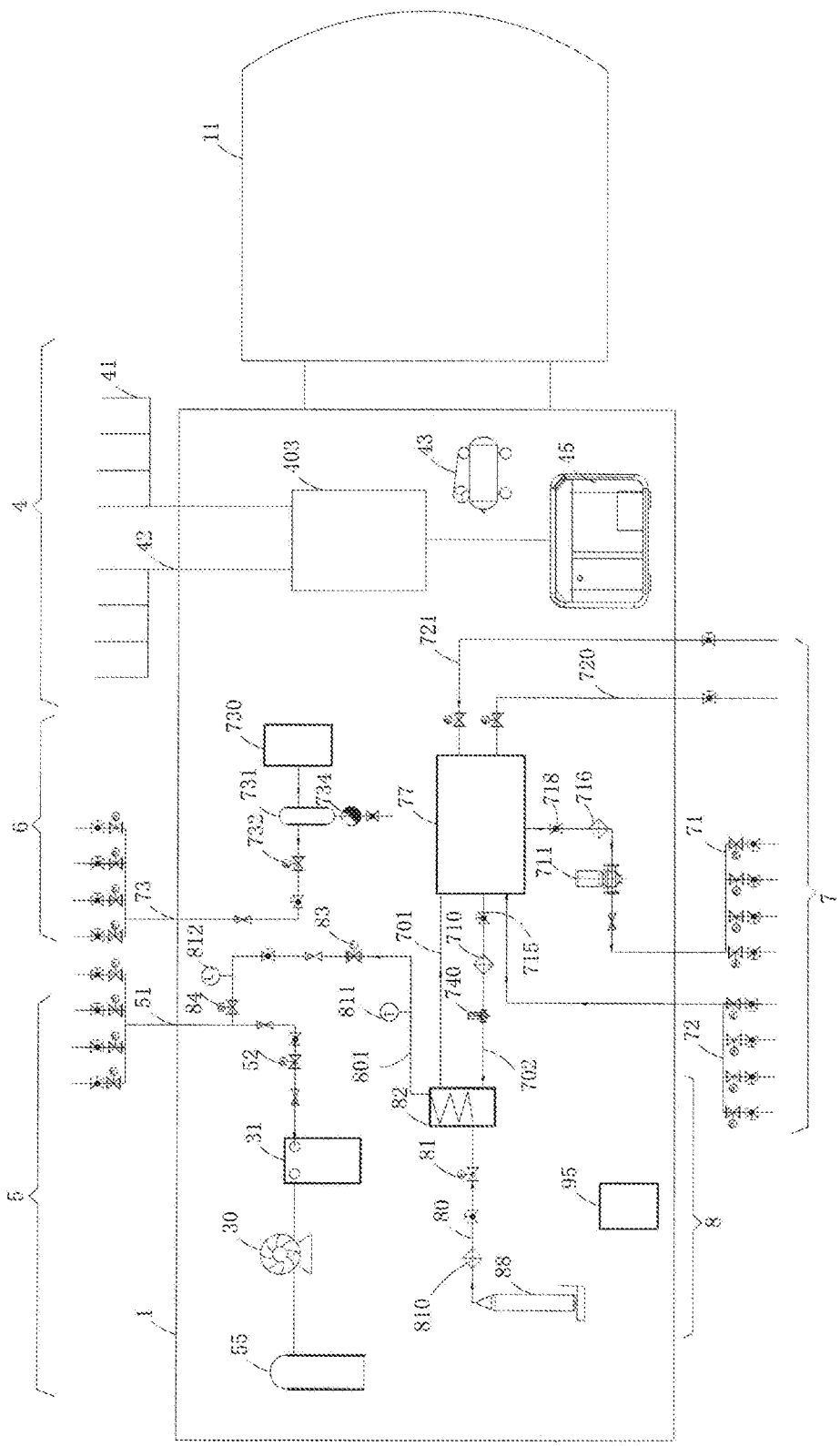
FIG. 3 is a schematic diagram of a mobile execution system in an embodiment.

FIG. 3 illustrates a mobile execution system that can be mounted on the vehicle body 1. The mobile execution system includes a power supply control system 4, a gas supply system 8, a sterilization gas processing system 5, a hydrothermal system 7, and a humidification system 6.

The power supply control system 4 includes a control system 403, an air compression device 43, and a power supply system 45. For example, the power supply system 45 can be a diesel generator.

The control system 403, the air compressor 43, and the power supply system 45 are disposed on the vehicle body 1 behind the cab 11. The power supply system 45 is used to supply power to electrical components in equipment such as the gas supply system 8, the sterilization gas processing system 5, the hydrothermal system 7, and the humidification system 6 of the small sterilization vehicle. The control system 403 is electrically connected to the electronic control components of the gas supply system 8, the sterilization gas processing system 5, the hydrothermal system 7, and the humidification system 6, controls the power switching and operation of each electronic control component, and is used to receive signals from various sensors. The air compressor 43 is used to provide pressurized air for a pneumatic ball valve (e.g., pneumatic ball valves 52, 81, or 732, and the like).

The gas supply system 8 includes a sterilization gas cylinder 88 (such as an ethylene oxide gas cylinder, or the like), a sterilization gas inlet pipeline 80, a filter 810, a gasifier 82, a sterilization gas outlet pipeline 801, a temperature sensor 811, a flow sensor 812, and a plurality of valves. The ethylene oxide gas cylinder 88, the filter 810, and the gasifier 82 are sequentially connected to the sterilization gas inlet pipeline 80, so that the gas inlet of the gasifier 82 is connected to the ethylene oxide gas cylinder 88 through the sterilization gas inlet pipeline 80. The temperature sensor 811 and the flow sensor 812 are sequentially connected to the sterilization gas outlet pipeline 801. The gas outlet of the gasifier 82 is connected to an end of the sterilization gas outlet pipeline 801, and the sterilization gas outlet pipeline 801 is used to output the sterilization gas. In the illustrated embodiment, the other end of the sterilization gas outlet pipeline 801 is connected to gas processing pipe 51, and shares the same set of connection branch pipes with the gas processing pipe 51. In other embodiments, the sterilization gas outlet pipeline 801 may be provided with a set of connection branch pipes for outputting the sterilization exhaust gas, and the gas processing pipe 51 may be provided with another set of connection branch pipes for inputting the sterilization exhaust gas. The sterilization gas pipeline in the gasifier 82 is folded or bent (or forms a spiral), and is connected to each of the sterilization gas inlet pipeline 80 and the sterilization gas outlet pipeline 801. A pneumatic ball valve 81 is disposed between the filter 810 and the gasifier 82, and an electric proportional valve 83 is disposed between the temperature sensor 811 and the flow sensor 812. A pneumatic ball valve 84 is disposed on the sterilization gas outlet pipeline 801 between the flow sensor 812 and the gas processing pipe 51.

The sterilization gas processing system 5 includes a gas processing device 55, a fan 30, a vacuum pump 31, a gas processing pipe 51, a pneumatic ball valve 52, and a plurality of other valves. The gas processing device 55, the fan 30, the vacuum pump 31, and the pneumatic ball valve 52 are sequentially connected to the gas processing pipe 51. One end of the gas processing pipe 51 is provided with a plurality of first connection branch pipes. The end of each first connection branch pipe is provided with a solenoid valve and a stop valve, which can provide the ethylene oxide gas for multiple small sterilization vehicles, or can receive the sterilization exhaust gas generated by multiple small sterilization vehicles.

By controlling the opening and closing of one or both of the pneumatic ball valve 52 and the pneumatic ball valve 84, the first connection branch pipe can be controlled to output the sterilization gas or to input the sterilization exhaust gas.

The hydrothermal system 7 includes a water inlet pipe 721, a water outlet pipe 720, a water heating tank 77, a water pump 711, a water pump 740, a filter 710, a hot water outlet pipe 71, and a hot water return pipe 72.

Water circulation pipes 701, 702 are provided between the water heating tank 77 and the gasifier 82. The water circulation pipe 702 is used to fill the gasifier 82 with hot water to gasify the sterilization gas flowing in the gasifier 82. The valve 715, the filter 710, and the water pump 740 are sequentially disposed in the water circulation pipe 702. The water circulation pipe 701 is used to recycle the hot water passing through the gasifier 82, by returning the hot water to the water heating tank 77. The water inlet pipe 721 and the water outlet pipe 720 are respectively connected to the upper and lower portions of the front wall of the water heating tank 77. The water inlet pipe 721 can be connected to an external water source (e.g., tap water, or the like), while the water outlet pipe 720 is used to exhaust the water heating tank 77. One end of the hot water outlet pipe 71 is connected to the bottom portion of the water heating tank 77. This end of the hot water outlet pipe 71 that is adjacent to the water heating tank 77 is provided with a filter 716 and a water pump 711. The filter 716 and a valve 718 are disposed between the water pump 711 and the water heating tank 77. One end of the hot water return pipe 72 is connected to the lower portion of the rear wall of the water heating tank 77. The connection end of the hot water outlet pipe 71 is provided with a third connection branch pipe, while the connection end of the hot water return pipe 72 is provided with a fourth connection branch pipe. Both ends of the third and fourth connection branch pipes are provided with solenoid valves and stop valves. The third connection branch pipe is used to connect a hot water inlet pipe 71 of the heat supply device 25 of the small sterilization vehicle (as shown in FIG. 2), and the fourth connection branch pipe is connected to a hot water return pipe 72 of the heat supply device 25 of the small sterilization vehicle (as shown in FIG. 2), thereby forming the water heating circulation circuit for the sterilization tank 2. The water heating tank 77 can heat the sterilization tank 2 of the small sterilization vehicle using hot water.

The humidification system 6 includes a humidification pipe 73, a hydrophobic valve 734, a pneumatic ball valve 732, a steam filter 731, and a steam generator 730. The pneumatic ball valve 732, the steam filter 731, and the steam generator 730 are disposed on the humidification pipe 73. The hydrophobic valve 734 is disposed on the bottom portion of the steam filter 731. One end of the humidification pipe 73 is provided with a plurality of second connection branch pipes. The end of each second connection branch pipe is provided with a solenoid valve and a stop valve, which can be used to humidify the sterilization tanks 2 of multiple small sterilization vehicles. The steam filter 731, the pneumatic ball valve 732, and a valve are disposed on the humidification pipe 73 between the steam generator 730 and the plurality of second connection branch pipes.

In the present embodiment, the hydrothermal system 7 is provided with the water heating tank 77, hot water is continuously supplied to the gas supply system 8 and the sterilization tank 2 of each of one or more small sterilization vehicles through the water pump 711 and the plurality of third connection branch pipes, and the gas supply system 8 and the sterilization tank 2 of each of the one or more small sterilization vehicles are heated by the hot water circulation, so that the sterilization gas is fully gasified and the sterilization tank 2 of each of the one or more small sterilization vehicles is kept at a constant temperature. The hot water heats the gas supply system 8 and the sterilization tank 2 through the circulation and then returns to the water heating tank for repeated use. At the same time, the water pipelines are provided with filters 710, 716 to filter the water. The steam generator 730 generates steam that is filtered through the steam filter 731, and that enters the interior chamber of the sterilization tank 2 of each of the one or more small sterilization vehicles to humidify each sterilization tank 2, which obtains an excellent humidification effect. The operation process can be automatically controlled and is easy to perform. Heating by the hot water and controlling by the control system allows improved safety of operation.

Figure 4:
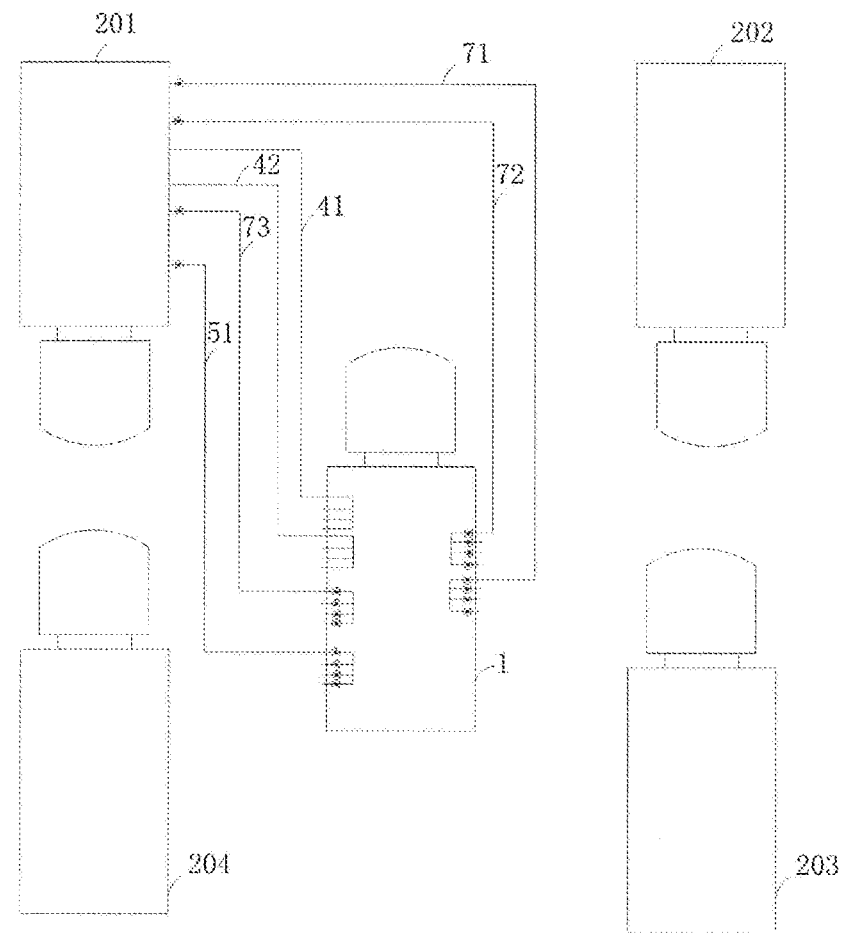
FIG. 4 is a schematic diagram illustrating the small sterilization vehicle of FIG. 2 connected to the mobile execution system of FIG. 3.

Referring to FIG. 4, the above-described mobile execution system can be connected to the one or more small sterilization vehicles through the plurality of first through fourth connection branch pipes.

According to some embodiments, one mobile execution system can be connected to 4 to 6 small sterilization vehicles. As shown in the non-limiting example of FIG. 4, one mobile execution system can be connected to four small sterilization vehicles 201, 202, 203, and 204 (each of which is shown, and described with respect to, FIG. 2).

When the mobile execution system is connected to the small sterilization vehicles, a sterilization process can be performed, which is similar to the method of using the mobile sterilization system described above with respect to FIG. 1.

Figure 5:
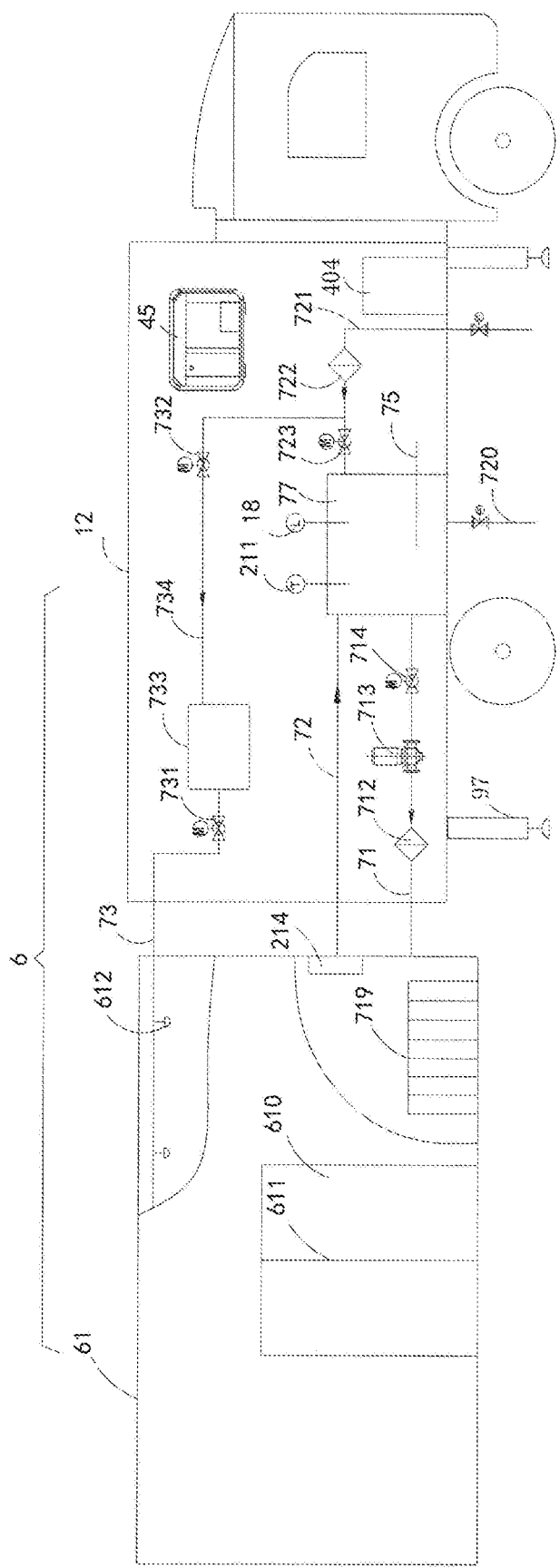
FIG. 5 is a schematic diagram of a mobile preprocessing system in an embodiment.

FIG. 5 illustrates a mobile preprocessing system according to an embodiment, which includes a first vehicle-mounted system and a detachable preprocessing chamber. The detachable preprocessing chamber is used to contain and pre-process items to be sterilized.

The first vehicle-mounted system includes a heating system, a humidification system 6, a control system 404, a water inlet system, and a vehicle-mounted system 12. The heating system, the humidification system 6, the control system 404, and the water inlet system are mounted on the vehicle-mounted system 12. The heating system, the humidification system 6, and the water inlet system are each electrically connected to the control system 404.

The detachable preprocessing chamber includes a preprocessing chamber frame 61, a temperature and humidity detector 214, a water heating plate 719, a sealing strip 611, a feed door 610, and a humidification spray head(s) 612. The temperature and humidity detector 214, the water heating plate 719, and the humidification spray head(s) 612 are mounted in the preprocessing chamber frame 61. The water heating plate 719 is located on the bottom portion of the preprocessing chamber frame 61, and is provided with a water-containing chamber. The humidification spray head(s) 612 is(are) mounted on the top portion of the preprocessing chamber frame 61. The preprocessing chamber frame 61 may be formed by a plurality of splicing plates. The feed door 610 is mounted on a side portion of the preprocessing chamber frame 61, and is sealed with the preprocessing chamber frame 61 by the sealing strip 611. The sealing strip 611 can be made of a thermoplastic rubber, which has the advantages of heat insulation, high temperature resistance, and good flexibility. The temperature and humidity detector 214 is electrically connected to the control system 404.

The heating system includes an electric heating pipe 75, a water heating tank 77, a temperature sensor 211, a liquid level sensor 18, a circulating water pump 713, a filter 712, a solenoid valve 714, and a water heating outlet pipe 71. The water outlet of the water heating tank 77 is sequentially connected to the solenoid valve 714, the circulating water pump 713, the filter 712, and the water heating plate 719 through the water heating outlet pipe 71. The water heating plate 719 is connected to the water inlet of the water heating tank 77. The solenoid valve 714 and the circulating water pump 713 are each electrically connected to the control system 404. The electric heating pipe 75 is inserted into the bottom portion of the water heating tank 77 and is electrically connected to the control system 404. The temperature sensor 211 and the liquid level sensor 18 are mounted on the upper portion of the side wall in the water heating tank 77, and are electrically connected to the control system 404. The water heating tank 77 is connected to the water inlet system through pipelines.

The humidification system 6 includes a humidification pipe 73, a solenoid valve 731, an atomizer 733, and a water supplementing pipe 734. One end of the water supplementing pipe 734 is connected to the water inlet system, and the other end of the water supplementing pipe 734 is sequentially connected to the atomizer 733, the solenoid valve 731, and the humidification pipe 73. The humidification pipe 73 is connected to the humidification spray head(s) 612. The solenoid valve 731 is electrically connected to the control system 404.

The water inlet system includes a water inlet pipe 721, a filter 722, a solenoid valve 732, and a solenoid valve 723. The filter 722 is mounted on the water inlet pipe 721, and the filter 722 is connected to the solenoid valve 732 and the solenoid valve 723 through pipelines. The solenoid valve 732 is connected to the water supplementing pipe 734 through the pipelines, while the solenoid valve 723 is connected to the water heating tank 77 through the pipelines. The solenoid valve 731 and the solenoid valve 732 are each electrically connected to the control system 404. The solenoid valve 732 and the solenoid valve 723 can be opened or closed as required, and their respective opening levels can also be adjusted.

A quick snap connector can be provided on the inlet of the water inlet pipe 721 to facilitate the connection with a water pipe of an external water source.

The preprocessing chamber frame 61 can be made of reusable thermal insulation materials. The wall of the preprocessing chamber can be formed by splicing plates, without the need for a pillar structure.

The vehicle-mounted system 12 may be loaded on a vehicle.

The first vehicle-mounted system and the detachable preprocessing chamber can be directly connected to each other by a flange.

The control system 404 is provided with a monitor, which can display the data monitored by the temperature and humidity detector 214 and the temperature sensor 211 in real time, and the control system 404 can perform parameter setting and program adjustment.

The atomizer 733 is provided with a pump-in pressure and a pump-out pressure, which allows the water entering the water supplementing pipe 734 to be pumped into the preprocessing chamber and atomized.

The electric heating pipe 75 is made of stainless steel, which is beneficial to prevent corrosion. The electric heating pipe 75 is connected to the control system 404 and a frequency converter, and the heating power of the electric heating pipe 75 is controlled by the control system 404.

The temperature sensor 211 is connected to the control system 404. The temperature measured by the temperature sensor 211 is transmitted to the control system 404, and the control system 404 controls the heating power of the electric heating pipe 75, thereby achieving the heating and temperature control of the water heating tank 77. After the water heating tank 77 reaches a predetermined temperature, a constant temperature can be maintained.

The water heating plate 719 comprises one of a copper-aluminum composite radiator or a steel-aluminum composite radiator, each of which has good corrosion resistance and heat conductivity, and can also save space.

Referring to FIG. 5, the present disclosure further provides a method of using the above-described mobile preprocessing system, and the method includes the following steps:

(1) The inlet of the water inlet pipe 721 is connected to an external source (e.g., a tap water source, or the like) using the quick snap connector, after the first mobile vehicle-mounted system reaches the designated location. The solenoid valve 723 is controlled to open and the other solenoid valves are controlled to close by the control system 404. The water heating tank 77 is filled with water from the external source (e.g., with tap water, or the like) by the water inlet pipe 721, and the water is filtered by the filter 722. The liquid level sensor 18 is used to monitor whether the water level reaches the predetermined position.

(2) After the water filling is completed, water from the external water source or supply is shut off, and the electric heating pipe 75 is controlled to activate, thereby heating the water in the water heating tank 77 to the predetermined temperature, and thereafter maintaining the water temperature at a range from 40° C. to 80° C.

(3) The preprocessing chamber is built. The modular splicing plates of the preprocessing chamber frame 61 and the feed door 610 that are carried within the first mobile vehicle-mounted system are assembled to form the preprocessing chamber, and then the temperature and humidity detector 214, the water heating plate 719, and the humidification spray head(s) 612 are mounted in the preprocessing chamber.

(4) The humidification spray head(s) 612 is(are) connected to the humidification pipe 73, and the water heating plate 719 is connected to the water heating outlet pipe 71 provided with the filter 712.

(5) The item to be sterilized is placed in the preprocessing chamber through the feed door 610, and then the feed door 610 is closed. The area between the door bodies of the feed door 610 and the area between the feed door 610 and the preprocessing chamber frame 61 are subsequently sealed with sealing strips 611.

(6) The heating and humidification process is performed, with the solenoid valve 723 controlled to be closed, with the solenoid valve 731, the solenoid valve 732, and the solenoid valve 714 controlled to be open, with the atomizer 733 and the circulating water pump 713 controlled to be on. This results in the water that is atomized by the atomizer 733 being sprayed into the preprocessing chamber to humidify the preprocessing chamber 61 by the humidification spray head(s) 612. This also results in the hot water in the water heating tank 77 being pumped by the circulating water pump 713, being filtered by the filter 712, being pumped into the water heating plate 719 to heat the preprocessing chamber, and then being pumped back through the water return pipe 72 to the water heating tank 77 to be reheated, thereby continuously and cyclically heating the preprocessing chamber 61 and maintaining the preprocessing chamber 61 at a constant temperature. The temperature and humidity in the preprocessing chamber are monitored in real time by the temperature and humidity detector 214, and if the monitored temperature is not within the limited range of between 40° C. and 80° C. and/or if the monitored humidity is not within the limited range of between 30% and 80%, the control system 404 would perform temperature and humidity adjustment accordingly.

(7) Various temperature and humidity levels are set according to the various items to be sterilized, and the items to be sterilized are pre-heated and pre-humidified, so as to increase the sterilization effect.

The above-described first vehicle-mounted system can provide heating, humidification, and automatic control for the preprocessing chamber. The preprocessing chamber can be assembled and disassembled, so that the sterilization pretreatment system can be flexibly moved, and the requirements for the site may be reduced. The entire preprocessing system can be quickly moved to the destination and then can be mounted and used immediately. The first vehicle-mounted system and the preprocessing chamber are mobile independent systems, which can be transported and used separately, or can be used together. The heating system adopts a manner of heating using hot water circulation, and the humidification system 6 adopts a manner of spraying using the atomizer 733, which allows the heating and humidification of the preprocessing chamber to be safe and efficient. At the same time, the control system 404 sets various preprocessing temperature and humidity settings according to requirements of the various items to be sterilized. The preprocessing chamber of the preprocessing system can be configured as a modular component, which can be detachably mounted for easy transportation. Therefore, the size of the preprocessing chamber can be adjusted according to the needs of sterilization. Since there is no intermediate support pillar, the space utilization of the preprocessing chamber can be improved. The preprocessing chamber frame uses reusable thermal insulation materials, which can save energy and can reduce costs, while ensuring the preprocessing effect.

Figure 6:
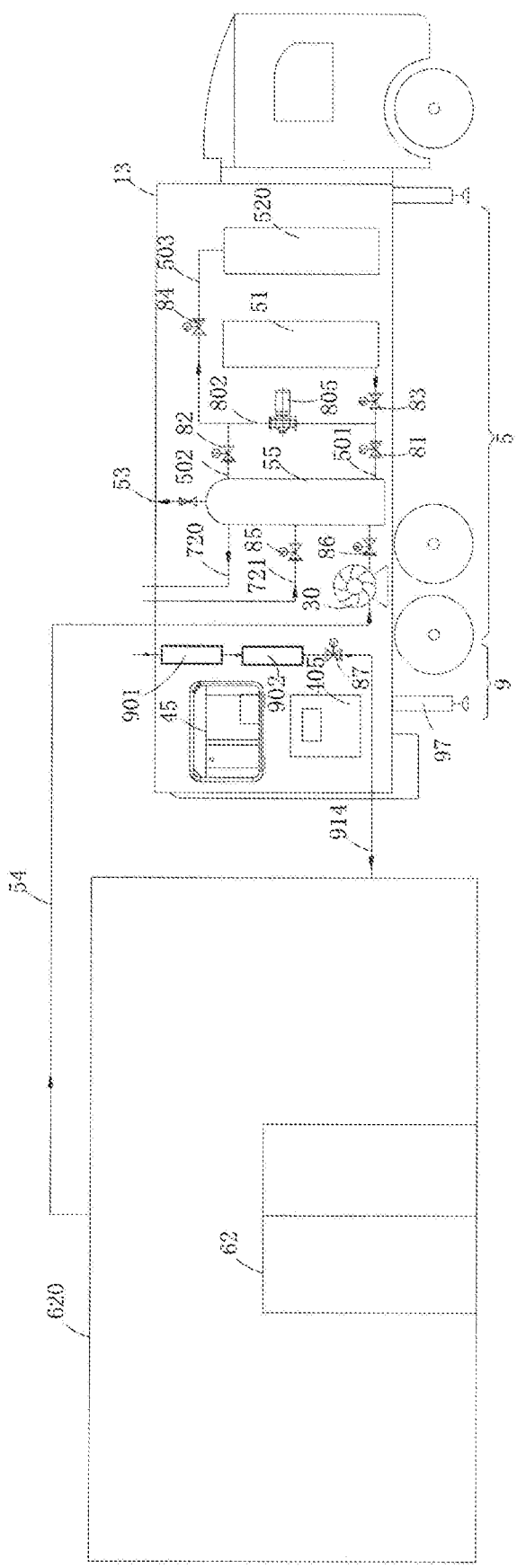
FIG. 6 is a schematic diagram of a mobile execution system in an embodiment.

FIG. 6 shows a mobile analysis system according to an embodiment, which includes a second vehicle-mounted system and an analysis chamber or detachable analysis chamber 620. The second vehicle-mounted system can be mounted on a vehicle, and the detachable analysis chamber 620 can be used to contain sterilized items.

The second vehicle-mounted system includes a control system 405, a power supply system 45, a vehicle-mounted system 13, a sterilization gas processing system 5, and a fresh air system 9. The control system 405, the power supply system 45, the sterilization gas processing system 5, and the fresh air system 9 are fixedly mounted on the vehicle-mounted system 13. The vehicle-mounted system 13 may be mounted on a vehicle. The power supply system 45, the sterilization gas processing system 5, and the fresh air system 9 are each electrically connected to the control system 405. The sterilization gas processing system 5 is connected to the detachable analysis chamber 620 through the exhaust pipe 54. The detachable analysis chamber 620 can be assembled and disassembled. The fresh air system 9 is connected to the detachable analysis chamber 620 through the gas inlet pipe 914. The sterilization gas processing system 5 includes a harmless gas processing device 55 including a tank body and a reaction liquid contained in the tank body. The specific implementation of the harmless gas processing device 55 is described in detail above with reference to the non-limiting embodiment of FIG. 1, or the like.

The detachable analysis chamber 620 includes a foldable support frame and a feed door 62. The feed door 62 is mounted on the sidewall of the foldable support frame, and the feed door 62 is sealed with the sidewall of the foldable support frame using a sealing strip, thus forming the detachable analysis chamber 620. The feed door 62 is a double-open door, and the sealing strip is located at the junction of each door and the foldable support frame.

The sterilization gas processing system 5 further includes a circulation pump 805, a fresh material storage tank 51, a waste liquid discharge pipe 503, a plurality of valves, and a fan 30. The fan 30 is connected to the detachable analysis chamber 620 through the exhaust pipe 54. The sterilization gas processing system 5 includes a gas outlet 53 on the top portion of the harmless gas processing device 55, a water outlet 720 on the upper portion of the harmless gas processing device 55, and a water inlet pipe 721 on the middle portion of the harmless gas processing device 55. A check valve is provided at the gas outlet 53. The fan 30 is connected to the bottom portion of the harmless gas processing device 55 through a valve 86, and the water inlet pipe 721 of the harmless gas processing device 55 is provided with a valve 85. A valve 81 and a valve 82 are mounted at the liquid outlet 501 and the liquid inlet 502 of the harmless gas processing device 55, respectively. The liquid outlet 501 and the liquid inlet 502 are connected to each other through a circulation pipe 802, and a circulation pump 805 is mounted on the circulation pipe 802. The fresh material storage tank 51 is connected between the valve 81 and the circulation pump 805 through a material supplementing pipe, and a valve 83 is mounted on the material supplementing pipe. The fresh material storage tank 51 is connected to the liquid inlet 502. A waste liquid recycle tank 520 is connected between the valve 82 and the circulation pump 805 through the waste liquid discharge pipe 503, and is connected to the liquid outlet 501. A valve 84 is mounted on the waste liquid discharge pipe 503. The fan 30, the circulation pump 805, the valve 81, the valve 82, the valve 83, the valve 84, the valve 85, and the valve 86 are each electrically connected to the control system 405. The harmless gas processing device 55 is provided with a hollow interlayer that is in communication with the water inlet pipe 721 and the water outlet 720.

The fresh air system 9 includes a gas inlet pipe 914, a primary efficiency air filter 901, a high efficiency air filter 902, and a valve 87. The gas inlet pipe 914 is sequentially connected to the primary efficiency air filter 901, the high efficiency air filter 902, and the valve 87. The valve 87 is connected to the detachable analysis chamber 620 through the gas inlet pipe 914. The valve 87 is electrically connected to the control system 405. The gas inlet pipe 914 may be disassembled separately during transportation and assembled together during use.

When the fan 30 is driven, an ethylene oxide analysis gas in the detachable analysis chamber 620 is transported to the harmless gas processing device 55 for harmless gas processing. When the harmless emission standard is obtained, the processed ethylene oxide analysis gas is discharged from the gas outlet 53. At the same time, the pumping action of the circulation pump 805 drives the air through the fresh air system 9 to provide sterile air to the detachable analysis chamber 620, which accelerates the gas flow in the detachable analysis chamber 620, and replaces any residual ethylene oxide analysis gas in the detachable analysis chamber 620, thereby shortening the analysis time. The sterilization gas processing system 5 can process and remove the ethylene oxide in the sterilization waste gas, so that the exhaust gas meets safety standards and causes no pollution to the environment.

The exhaust pipe 54 is connected to the top portion of the detachable analysis chamber 620. The gas inlet pipe 914 is connected to the bottom portion of the detachable analysis chamber 620.

The mobile analysis system includes the vehicle-mounted system and the analysis chamber that are independently disposed and carried, which allows the storage, use, and transportation to be more convenient, and the use of ethylene oxide sterilization technology to be expanded, so that the mobile analysis system can be used in conjunction with the ethylene oxide sterilizer to sterilize items and to analyze the residual ethylene oxide in the sterilized items. Therefore, a fully automated harmless gas processing and a rapid analysis of the residual ethylene oxide of sterilized items are realized, which is suitable for all-weather environments and meets the large demand for sterile products for disaster and epidemic prevention. The second vehicle-mounted system undertakes the analysis and processing tasks of the ethylene oxide gas. The gas in the analysis chamber 620 is evacuated and replaced by the fan 30 and the fresh air system 9, so that the analysis of residual ethylene oxide on sterilized items can be promoted by increasing the amount of ventilation, and the processing speed of the sterilized items to reach the standard for safe use is increased. In addition, the residual ethylene oxide that has been evacuated is processed using the harmless gas processing to be discharged after meeting the environmental safety discharge standards, thereby ensuring the safety of the environmental and living beings.

Referring to FIG. 6, the present disclosure further provides a method of using the above-described mobile analysis system, and the method includes the following steps:

(1) The second vehicle-mounted system is transported to the sterilization work site using the vehicle-mounted system 13, and the detachable analysis chamber 620 is built nearby. When starting the analysis work, the power supply system 45 is switched on. Under the control of the control system 405, the fan 30, the valve 81, the valve 82, the valve 85, the valve 86, the valve 87, and the circulating pump 805 are switched on or opened, as appropriate, resulting in the ethylene oxide analysis gas in the detachable analysis chamber 620 being drawn into the harmless gas processing device 55 by the fan 30.

(2) The ethylene oxide analysis gas in the detachable analysis chamber 620 is drawn out and the air pressure is reduced. Under the effect of the pressure difference, the air from the fresh air inlet enters, and is filtered by the primary efficiency air filter 901 and the high efficiency air filter 902 to generate sterile air, which flows into the detachable analysis chamber 620 to complete the gas replacement.

(3) The harmless gas processing of the ethylene oxide analysis gas is performed in the harmless gas processing device 55. The valve 83 and the valve 84 are in the closed state at this time, and the circulation pump 805 circulates the reaction liquid in the harmless gas processing device 55 through the circulation pipeline 802, and the processed harmless gas is discharged from the gas outlet 53. When the harmless gas processing device 55 is in operation, cooling water enters the hollow interlayer of the harmless gas processing device 55 through the water inlet pipe 721 and the valve 85 to cool the harmless gas processing device 55, and eventually flows out through the water outlet 720.

(4) Steps (1) to (3) are repeated until the concentration of the residual ethylene oxide on the sterilized items in the analysis chamber 620 reaches safe levels under the relevant standards. At that point, the fan 30, the valve 81, the valve 82, the valve 85, the valve 86, the valve 87, the circulation pump 805, and the power supply system 45 are turned off or closed, as appropriate, thereby terminating a round of analysis.

(5) After several rounds of analysis, the reaction liquid in the harmless gas processing device 55 is completely consumed. At this point, the circulation pump 805, the valve 81, and the valve 84 are turned on or opened, as appropriate, thereby drawing the reaction waste liquid that is in the harmless gas processing device 55 into the waste liquid recovery tank 520 through the circulation pipeline 802, the waste liquid discharge pipe 503, and the liquid outlet 501. Thereafter, the valve 81 and the valve 84 are closed, thereby completing the waste liquid discharge. The valve 82 and the valve 83 are subsequently opened, resulting in the pumping of fresh reaction liquid that is in the fresh material storage tank 51 into the harmless gas processing device 55 through the material supplementing pipe and the circulation pipeline 802. After the desired amount of fresh reaction liquid has been pumped into the harmless gas processing device 55, the circulation pump 805, the valve 82, and the valve 83 are turned off or closed, as appropriate, thereby completing the fresh liquid filling.

Thereafter, steps (1) to (4) are repeated as desired or as appropriate.

Figure 7:
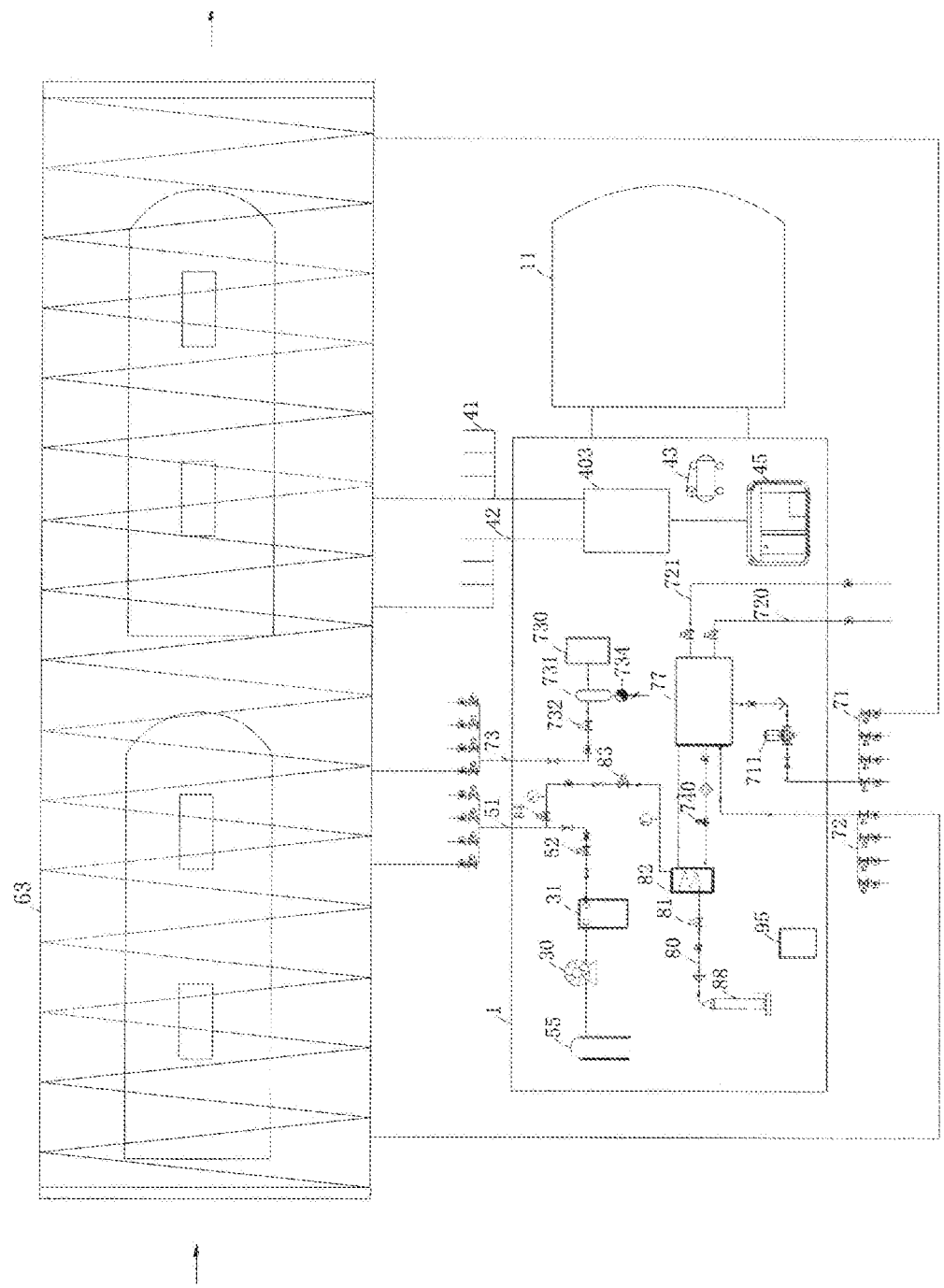
FIG. 7 is a schematic diagram of a mobile execution system connected to a foldable sterilizer in an embodiment.
Figure 8:
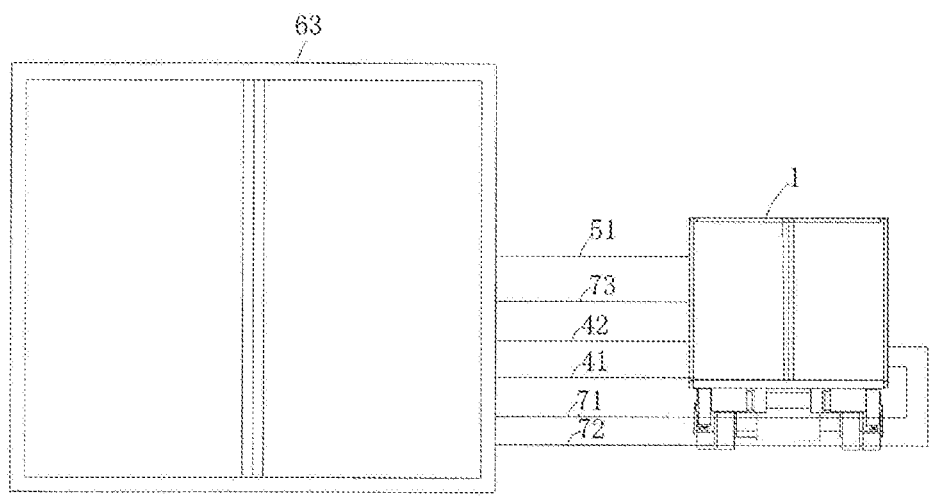
FIG. 8 is a schematic diagram of the mobile execution system connected to the foldable sterilizer of FIG. 7 viewed from another perspective.

Referring to FIGS. 7 and 8, the mobile execution system and a foldable sterilizer 63 are similarly connected to each other through the plurality of first through fourth connection branch pipes. The foldable sterilizer 63 can be assembled, disassembled, folded, and transported with the mobile execution system. The mobile execution system can heat the foldable sterilizer 63 through the hot water outlet pipe 71, and the hot water returns to the water heating tank 77 of the mobile execution system through the hot water return pipe 72. The mobile execution system can humidify the foldable sterilizer 63 through the humidification pipe 73. The mobile execution system can transmit control signals to the foldable sterilizer 63 and can receive feedback signals through the signal line 41, and can supply power to the foldable sterilizer 63 through the electric transmission line 42.

It should be noted that the valves mounted on pipes in the present disclosure can be mounted with one, two, or more valves as needed, and, according to the usage, each valve can be one of a stop valve, a flow control valve, a check valve, or a hand valve, etc. In some cases, each valve can be a solenoid valve, so that the opening and closing of the valve can be controlled automatically, and the degree of the opening can also be adjusted automatically.

The technical solution provided by the present disclosure can achieve the following effects:

1. The sterilization method can be configured according to specified requirements, has an excellent and broad-spectrum sterilization effect, and can kill pathogenic microorganisms on the surface and inside of all items.

2. The mobile preprocess, sterilization, and analysis devices have the advantage of flexibility, quickness, and reliability, and can be quickly moved to the destination and used immediately.

3. The process of harmless gas preprocessing for the sterilization gas is fast, safe, reliable, and pollution-free.

4. A variety of sterilization vehicles and sterilizers can be configured, and the sterilization range is large.

5. It can be widely used for major epidemics, natural disasters (such as, earthquakes, floods, and the like), or disease prevention and control in sports events and public places. It can also be used for emergency treatment of biosecurity incidents, as well as disinfection or sterilization of contaminated items, wastes, and garbage, such as medical supplies, surgical instruments, instruments, and equipment involved in medical services.

In summary, the present disclosure fills in the gaps in mobile on-site pre-heating and pre-humidification, low-temperature sterilization, and analysis processing. The technical solutions disclosed in the present disclosure are flexible, mobile, and suitable for on-site applications, and have the advantage of wide coverage, large processing scale, low sterilization temperature, high efficiency, wide spectrum, and fast sterilization. Moreover, the technical solutions herein are compatible with the environment, and have reliable effects and wide applications. In particular, in public health events caused by pathogenic microbial infections, the technical solutions of the present disclosure can quickly and efficiently solve the problem of epidemic prevention and control, can cut off the source of infection, and can effectively prevent the spread of viruses.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A mobile sterilization system, comprising:
a vehicle body;
a sterilization system, comprising:
    a sterilization tank configured to contain an item to be sterilized, wherein the sterilization tank comprises an interior chamber and a sealing door through which the item enters and exits the interior chamber, and wherein, when the sealing door is closed with the item in the interior chamber, the sterilization tank encloses the item to allow the item to be sterilized using a sterilization gas, and
    a heat supply device comprising a heating chamber surrounding the sterilization tank;
a hydrothermal system, comprising:
    a water heating tank connected to the heating chamber of the heat supply device through a hot water outlet pipe and a hot water return pipe;
a gas supply system, comprising:
    a sterilization gas source, and
    a gasifier, wherein a gas inlet of the gasifier is connected to the sterilization gas source through a sterilization gas inlet pipeline, a gas outlet of the gasifier is connected to the sterilization tank through a sterilization gas outlet pipeline, and a water circulation pipe is provided between the gasifier and the water heating tank;

a gas processing system, comprising:
  a first fan,
  a vacuum pump, and
  a gas processing device,
  wherein an inlet of the gas processing device is connected to the sterilization tank through a gas processing pipe, the first fan and the vacuum pump are mounted on the gas processing pipe, and the gas processing device is configured to process a sterilization exhaust gas that is input from the gas processing pipe;

a humidification system, comprising:
  a steam generator, wherein a gas outlet of the steam generator is connected to the sterilization tank through a humidification pipe; and a fresh air system, comprising:
  an air inlet pipeline connected to the sterilization tank, and
  an air filter mounted on the air inlet pipeline;

wherein the sterilization system, the hydrothermal system, the gas supply system, the gas processing system, the humidification system, and the fresh air system are mounted on the vehicle body.

2. The mobile sterilization system of claim 1, wherein the sterilization tank is provided with a first vent and a second vent, the first vent and the second vent are connected to each other by a gas circulation pipe provided with a second fan, and the gas processing pipe is connected to the gas circulation pipe.

3. The mobile sterilization system of claim 2, wherein a first control valve is mounted on the gas circulation pipe and is located downstream of an airflow of the second fan, and the gas processing pipe is connected to the gas circulation pipe and is located upstream of the second fan.

4. The mobile sterilization system of claim 1, wherein the sterilization tank is provided with one or more sensors, the one or more sensors comprising at least one of a temperature sensor, a humidity sensor, a pressure sensor, or a sterilization gas concentration sensor.

5. The mobile sterilization system of claim 1, wherein the humidification pipe is provided with a steam filter.

6. The mobile sterilization system of claim 1, wherein the air inlet pipeline is further provided with a first electric proportional valve and a first pneumatic ball valve, and the mobile sterilization system further comprises an air compression device configured to provide a pressure to the first pneumatic ball valve.

7. The mobile sterilization system of claim 1, wherein the gas supply system further comprises a filter, a temperature sensor, a flow sensor, a second pneumatic ball valve, and a second electric proportional valve; the filter and the second pneumatic ball valve are sequentially connected to the sterilization gas inlet pipeline; the temperature sensor, the second electric proportional valve, and the flow sensor are sequentially connected to the sterilization gas outlet pipeline; a sterilization gas flow pipeline in the gasifier is folded, bent, or spiral; and the second pneumatic ball valve is provided between the filter and the gasifier.

8. The mobile sterilization system of claim 1, wherein a liquid absorption filler and a solid absorption filler are provided in the gas processing device, the liquid absorption filler is a solution obtained by mixing oleic acid, sulfated castor oil, sodium chloride, potassium hydroxide, and calcium hydroxide with a molar ratio of 1:1:0.01:0.01:0.01, and the solid absorption filler is activated carbon.

9. The mobile sterilization system of claim 1, wherein the hydrothermal system further comprises a water inlet pipe, a water outlet pipe, a first water pump, and a second water pump; the water inlet pipe and the water outlet pipe are each connected to the water heating tank; the hot water outlet pipe and the hot water return pipe are connected between the heat supply device and the water heating tank to form a water heating circulation circuit; the first water pump is disposed on an end of the water heating tank adjacent to the hot water outlet pipe; the water circulation pipe is disposed between the water heating tank and the gasifier; and the second water pump is disposed in the water circulation pipe.

10. The mobile sterilization system of claim 1, further comprising a constant temperature incubator that performs a constant temperature incubation for an ethylene oxide sterilization biological indicator provided in the sterilization tank and that detects presence of a sterilization effect.

11. The mobile sterilization system of claim 1, further comprising a generator and a control system, wherein the generator is configured to supply power to the hydrothermal system, the gas supply system, the gas processing system, the humidification system and the fresh air system, and the control system is configured to control at least one of the hydrothermal system, the gas supply system, the gas processing system, the humidification system, or the fresh air system to perform one or more functions.

* * * * *